(12) United States Patent
Kjaer et al.

(10) Patent No.: US 10,111,969 B2
(45) Date of Patent: Oct. 30, 2018

(54) UPAR TARGETING PEPTIDE FOR USE IN PEROPERATIVE OPTICAL IMAGING OF INVASIVE CANCER

(71) Applicant: RIGSHOSPITALET, Copenhagen (DK)

(72) Inventors: Andreas Kjaer, Frederiksberg (DK); Morten Persson, Copenhagen (DK)

(73) Assignee: RIGSHOSPITALET, Copenhagen (DK)

( * ) Notice: Subject to any disclaimer, the term of this patent is extended or adjusted under 35 U.S.C. 154(b) by 0 days.

(21) Appl. No.: 15/512,276

(22) PCT Filed: Sep. 3, 2015

(86) PCT No.: PCT/DK2015/050261
§ 371 (c)(1),
(2) Date: Mar. 17, 2017

(87) PCT Pub. No.: WO2016/041558
PCT Pub. Date: Mar. 24, 2016

(65) Prior Publication Data
US 2017/0304468 A1    Oct. 26, 2017

(30) Foreign Application Priority Data

Sep. 17, 2014 (DK) .................... 2014 70573

(51) Int. Cl.
*A61B 10/00* (2006.01)
*A61B 5/00* (2006.01)
*A61B 8/00* (2006.01)
*A61K 49/00* (2006.01)

(52) U.S. Cl.
CPC ...... *A61K 49/0056* (2013.01); *A61K 49/0034* (2013.01)

(58) Field of Classification Search
CPC ............... A61K 49/00; A61K 49/0056; A61K 49/0034; A61K 2123/00; A61K 2121/00

USPC .... 424/1.11, 1.65, 1.81, 1.85, 1.89, 9.1, 9.2, 424/9.6; 514/1, 1.1, 19.2, 19.3, 19.4, 514/19.5, 19.6, 21.6; 530/300, 328, 333, 530/338

See application file for complete search history.

(56) References Cited

U.S. PATENT DOCUMENTS 8,568,689 B1 * 10/2013 Cuthbertson ........ A61K 51/088
424/1.11
2004/0204348 A1    10/2004 Jones et al.

FOREIGN PATENT DOCUMENTS

| WO | WO 98/47541 A1 | 10/1998 |
| WO | WO 2005/058370 A1 | 6/2005 |
| WO | WO 2005/058372 A1 | 6/2005 |
| WO | WO 2006/036071 A2 | 4/2006 |
| WO | WO 2013/167130 A1 | 11/2013 |
| WO | WO 2014/086364 A1 | 6/2014 |

OTHER PUBLICATIONS

International Search Report and Written Opinion for corresponding International Patent Application No. PCT/DK2015/050261 dated Dec. 7, 2015, 20 pages.
Handgraaf et al., "Real-time near-infrared fluorescence guided surgery in gynecologic 3 oncology: A review of the current state of the art," Gynecologic Oncology, (2014).

* cited by examiner

*Primary Examiner* — D. L. Jones
(74) *Attorney, Agent, or Firm* — Merchant & Gould P.C.

(57) ABSTRACT

There is provided a novel conjugate that binds to the cell surface receptor uPA (uPAR). The conjugate is based on a fluorescence-labeled peptide useful as a diagnostic probe to the surfaces of cells expressing uPAR. The conjugate is capable of carrying a suitable detectable and imageable label that will allow qualitative detection and also quantitation of uPAR levels in vitro and in vivo. This renders the surgical resection of tumors more optimal.

3 Claims, 5 Drawing Sheets

UPAR TARGETING PEPTIDE FOR USE IN PEROPERATIVE OPTICAL IMAGING OF INVASIVE CANCER

This application is a National Stage Application of International Patent Application No. PCT/DK2015/050261, filed 3 Sep. 2015, which claims benefit of Serial No. PA 2014 70573, filed 17 Sep. 2014 in Denmark and which applications are incorporated herein by reference. To the extent appropriate, a claim of priority is made to each of the above disclosed applications.

FIELD OF THE INVENTION

The present invention relates to a novel conjugate that binds to the cell surface receptor urokinase-type plasminogen activator receptor (uPAR). More specifically the conjugate is based on a fluorescence-labeled peptide useful as a diagnostic probe to the surfaces of cells expressing uPAR. The conjugate of the invention is capable of carrying a suitable detectable and imageable label that will allow for clear tumor delineation both in vitro and in vivo. This renders the surgical resection of tumors more optimal.

BACKGROUND OF THE INVENTION

When performing cancer surgery with intent of radically remove cancer and metastases, delineation of active tumour is a major challenge and accordingly, either cancer tissue is left behind with poor prognosis or to ensure radical surgery, unnecessary extensive surgery is performed with removal of substantial amounts of healthy tissue.

Developments in the area of improved methods for cancer resection have in many years been stagnant. A surgeon's finest task is still to differentiate between healthy and diseased tissue under white light illumination. This can in many cases be difficult due to hidden areas of diseased tissue. In cancer treatment the best prognosis comes with complete removal of the cancerous tissue [1, 2]. Today the gold standard for assuring optimal resection is to take histological samples in the tumor bed and test for positive tumour margins. Several studies have shown this to be both inaccurate and time consuming.

Intraoperative optical imaging is a new emerging technique that allows the surgeon to differentiate between healthy and diseased tissue with help from a targeted optical probe [3, 4]. Near Infrared (NIR) florescence-imaging is a newer technique that can be used in intraoperative optical imaging. NIR fluorescence has some advantages compared to other widely used fluorophors with lower wavelength maxima. Tissue penetration is one of the forces of NIR fluorophors (NIRFs. Moreover, tissue autoflourescence is minimised in the NIR range and therefore enhance the tumour to background ratio needed for intraoperative imaging. These properties make NIRFs ideal for intraoperative surgery.

In neurosurgical oncology, fluorescence to guide surgery of high-grade glioblastoma has already been investigated [1]. The current fluorescence guided surgery (FGS) use ALA induces PpIX fluorescence which utilise the PpIX produced in all mammal cells. However a significant higher production of PpIX is found in tumour cells (14-17 pogue et all 2010). Even though this system delineates the tumour with success, the system still has its drawbacks. Therefore, a clear clinical need for more specific targeting with NIRFs has evolved.

Urokinase-type plasminogen activator receptor (uPAR) is frequently over expressed in many cancer types. Expression of uPAR is associated with metastatic disease and poor prognosis and the receptor is often located in excess in the invasive front of the tumour. This makes uPAR ideal as a targeted probe for intraoperative optical imaging. A well validated uPAR targeted peptide AE105 has been used extensively in PET imaging for targeting uPAR previously by our group [5-8].

Recently, optical imaging using fluorescence was introduced to help delineating tumors. One example is indocyanin green (ICG) that to some extent unspecifically leaks out into tumors due to vascularization and leaky vessels. However, the unspecific nature of the methods limits its value.

Handgraaf et al [15] recognize that ICG is a non-targeted dye and its chemical structure does not allow conjugation to tumor specific ligands.

WO2014/086364 and WO2013/167130 disclose the use of radionuclide-labelled uPAR binding peptides for PET-imaging of cancer diseases. Such compounds were coupled via a chelating agent to a radionuclide.

Hence, there is a need for an improved imaging probe for guided surgery.

SUMMARY OF THE INVENTION

The present inventors have surprisingly conjugated AE105 with indocyanine green (ICG). Due to the relatively large size and high hydrophobicity of ICG, two glutamic acid was used as a linker between AE105 and ICG (FIG. 1), thus providing minimal interference between AE105 and ICG. This novel fluorescent probe AE105-Glu-Glu-ICG has unexpectedly shown both in vitro and in vivo potential for use in fluorescent-guided cancer resection. It is to be noted that the prior art does not focus on the fluorophor labelled uPAR-targeting peptide conjugate although the prior art discloses radionuclide-labelled uPAR binding peptides.

Accordingly, the novel probe AE105-Glu-Glu-ICG enables a whole new concept where targeted optical imaging of the invasive cancer cells uses the proteolytic system receptor uPAR as a target. The major advantages are that it is tumour specific and that it particularly accumulates in the invasive front of cancers. Accordingly, it is clearly indicating where the active border of a tumour is relative to surrounding healthy tissue. In this way, the surgeon can exactly see where the tumour stops and remove only the tumour. If no tissue lightening up is left behind the cancer was successfully removed.

In accordance with the present invention there is therefore provided a novel fluorophor labelled uPAR-targeting peptide conjugate having the formula:

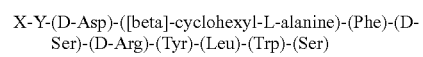

X-Y-(D-Asp)-([beta]-cyclohexyl-L-alanine)-(Phe)-(D-Ser)-(D-Arg)-(Tyr)-(Leu)-(Trp)-(Ser)

wherein,

X represents imageable moiety capable of detection either directly or indirectly in a optical imaging procedure, and Y represents a spacer, a biomodifier or is absent.

Particularly preferred are conjugates having the formula

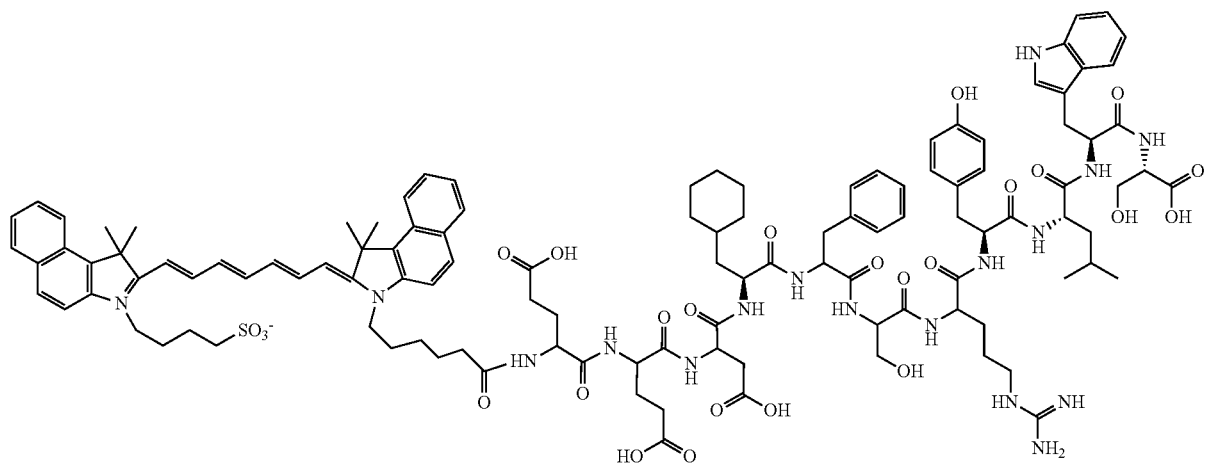

The compounds are preferably for use in fluorescence guided surgical resection of tumours. In this respect the compounds are administered to a subject in a dose of 0.1-100 mg per person. In such an application it is very suitable for peroperative optical imaging of cancer.

The present invention also provides a pharmaceutical composition for optical imaging of cancer, wherein the composition comprises a compound of the invention together with at least one pharmaceutically acceptable carrier or excipient. The dose of the compound is preferably 0.1-100 mg per person.

The invention also encompasses the use of the compound for the manufacture of a diagnostic agent for use in a method of optical imaging of metastatic cancer involving administration of said compound to a subject and generation of an image of at least part of said subject.

In a further aspect there is provided a method of optical imaging of cancer of a subject involving administering the compound of the present invention to the subject and generating an optical image of at least a part of the subject to which said compound has distributed.

DETAILED DESCRIPTION OF THE INVENTION

Concerning the synthesis of the peptides used in the present invention reference is made to U.S. Pat. No. 7,026,282.

The peptide/chelate conjugates of the invention are labelled by reacting the conjugate with radionuclide, e.g. as a metal salt, preferably water soluble. The reaction is carried out by known methods in the art.

EXAMPLE

Figure 1:
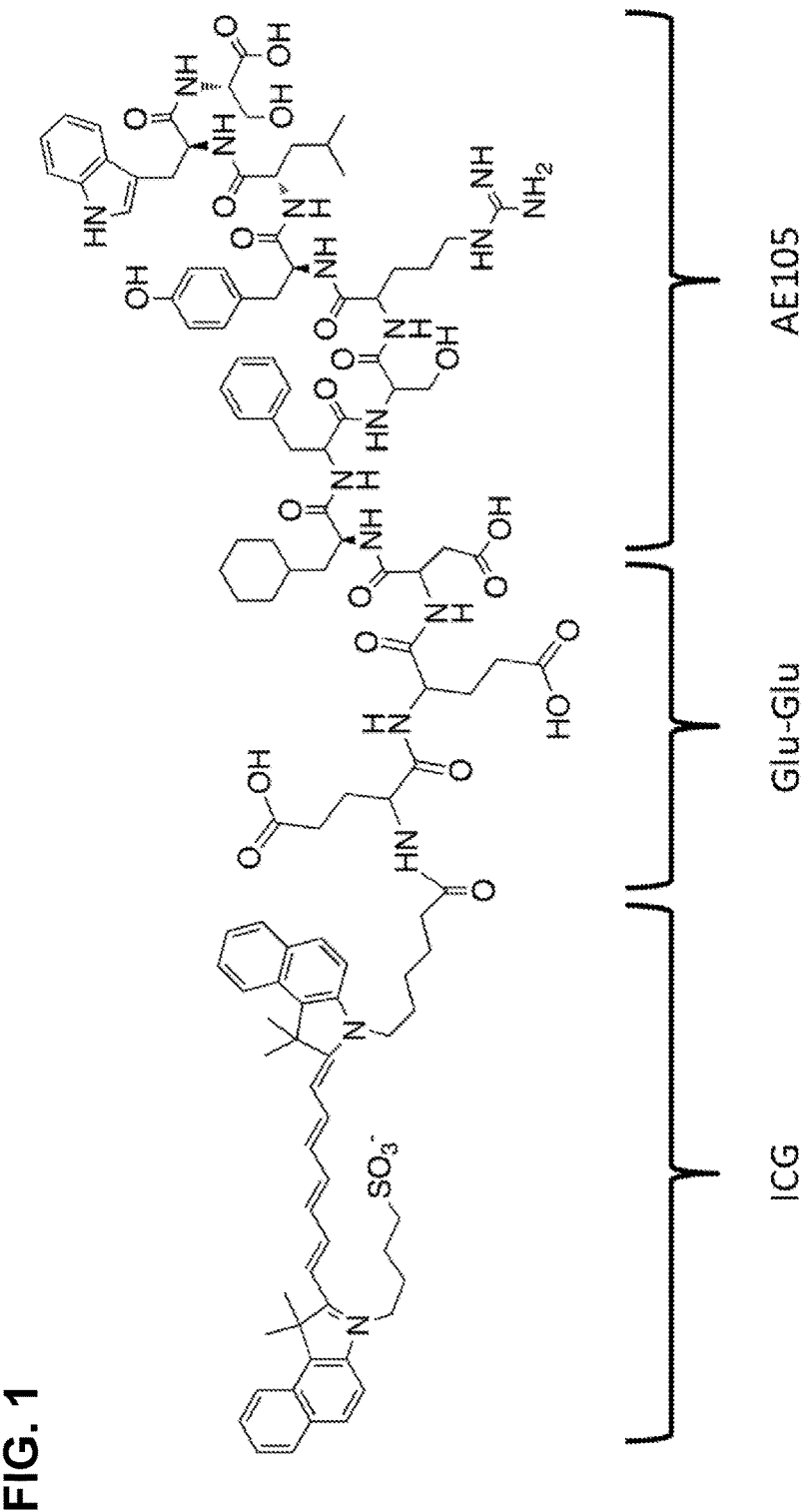
FIG. 1 shows the structural formula of the compound of the present invention with indications of peptide and fluorophor part.

The peptide AE105 (Asp-Cha-Phe-Ser-Arg-Tyr-Leu-Trp-Ser-OH) was synthesized by standard solid-phase peptide chemistry. The peptide AE105 was conjugated to ICG (4-(2-((1E,3E,5E,7Z)-7-(3(5-carboxypentyl)-1,1-dimethyl-1H-benzo[e]indol-2(3)-ydlidene) hepta-1,3,5-trienyl)-1,1di-methyl-1H-benzo-[e]indolium-3-yl)butane-1-sulfonate) with two glutamic acids as linker (ICG-Glu-Glu-AE105); see FIG. 1. The probe has a final weight of 2197.55 g/mol. For in vivo injection ICG-Glu-Glu-AE105 was dissolved in (2-hydroxypropyl)-β-cyclodextrin with 2% DSMO.

Cell Lines

Human glioblastoma cell line U87MG was purchased from the American Type Culture Collection and culture media was obtained from Invitrogen. U87MG was cultured in DMEM added 10% FBS and 1% PenStrep. When the cells reached 70-80% confluency the cells were harvested.

All animal experiments were performed under a protocol approved by the Animal Research Committee of the Danish Ministry of Justice. $5*10^6$ U87MG cells were suspended in 200 ul PBS and inoculated on both flanks of the mouse. When the tumours reached an appropriate size the mice were imaged with AE105-Glu-Glu-ICG.

Flowcytometry

After harvesting of cells were washed in buffer and stained with either an in-house produced antibody (3 μg/ml), IgG isotype (3 g/ml; 14-4714 eBioscience) or blank control for 1 hr in 4° C. on a shaking table. The cells were washed 3 times with buffer and then stained with a secondary antibody (goat-anti-mouse-PE 1/500) for 30 min in 4° C. on a shaking table. The result was analysed on the BD FAC-SCanto cell analyser.

ELISA Assay

Tumours were homogenised and a suspension containing the tumor lysate were stored at −80° C. The plate was coated with an anti uPAR antibody R2 (3 μg/ml) overnight at 4° C. After this incubation 2% BSA was added for 5 min and the plate was washed with buffer. uPAR standard (10 ng/ml) or tumor lysate (diluted 1:20) was added and incubated for 2 hr in RT and washed with buffer. A primary antibody (rabbit-anti-uPAR, 1 μg/ml) was added to the well and incubated for 30 min in RT and washed. A secondary HRP conjugated anti-rabbit antibody was added (diluted 1:2500) and incubated for 30 min in RT and washed. The bound HRP conjugated antibody was quantified by adding 4 OPD tablets (Dako #S2045) in 12 ml water and 10 µl $H_2O_2$. The reaction was stopped with 1M $H_2SO_4$ when the proper coloration of the well was present. An ELISA reader was used to analyze the plate at 490 nm and 650 nm as reference.

Optical Imaging

The mice were injected with 10 nmol of AE105-Glu-Glu-ICG or ICG i.v., and imaged 15 hr post injection. Before scan the mice were anaesthetized with 2% isofluran and positioned in a prone position. For imaging the IVIS Lumina XR and the acquisition software Living Image were used. The excitation filter was set to 710 nm and the emission filter was set in the ICG position. Acquisition was set to auto-settings to achieve the best acquisition as possible.

After imaging with IVIS Lumina XR the mouse were moved to a Fluobeam setup and imaged with appropriate acquisition time.

The TBR values were calculated by drawing a ROI over each tumor and place the background ROI in an area with constant background signal.

Results

In the production of the novel uPAR targeted fluorescence probe of the present invention two glutamic acids were introduced as linkers to partly reduce a potential interaction between ICG and the binding affinity of AE105 toward uPAR. The results indeed revealed a reduction in the binding affinity towards purified uPAR for ICG-Glu-Glu-AE105 ($IC_{50} \approx 80$ nM) compared to AE105 ($IC_{50} \approx 10$ nM), however the probe surprisingly retained sufficient affinity for guided surgical procedures.

Figure 2:
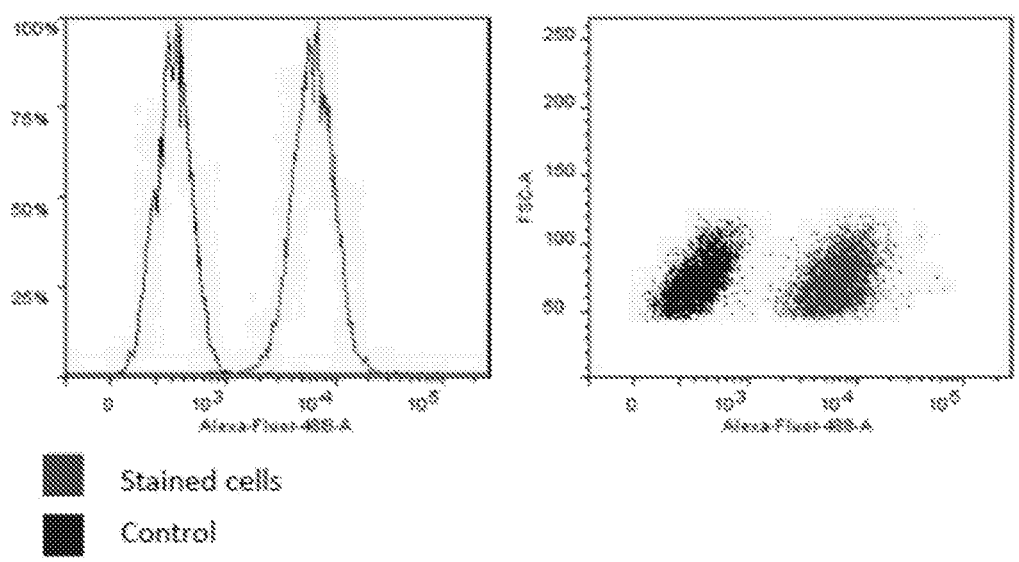
FIG. 2 shows staining experiments with rabbit-anti-uPAR.

Before any in vivo experiments were initiated, with U87MG cancer cells the expression of uPAR was measured in vitro by flowcytometry. The staining with rabbit-anti-uPAR showed a clear rightshift in fluorescence compared to the control, thus confirming high level of uPAR expression (FIG. 2a). The expression of uPAR was also investigated on histological samples from tumors grown for 5 weeks in vivo using IHC staining (FIG. 2b). An intense staining for uPAR expression was found, thus confirming the result from flowcytometry.

Figure 3:
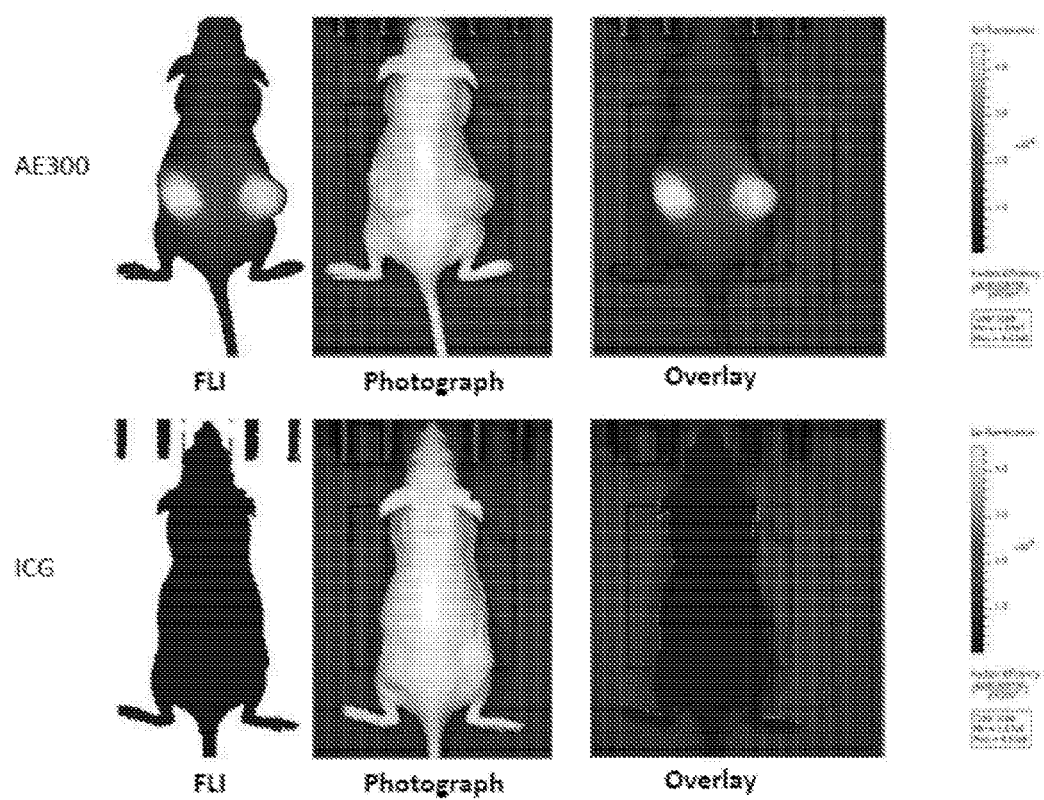
FIG. 3 shows photographs of tumor scans with the compound of the invention and with ICG.
Figure 4:
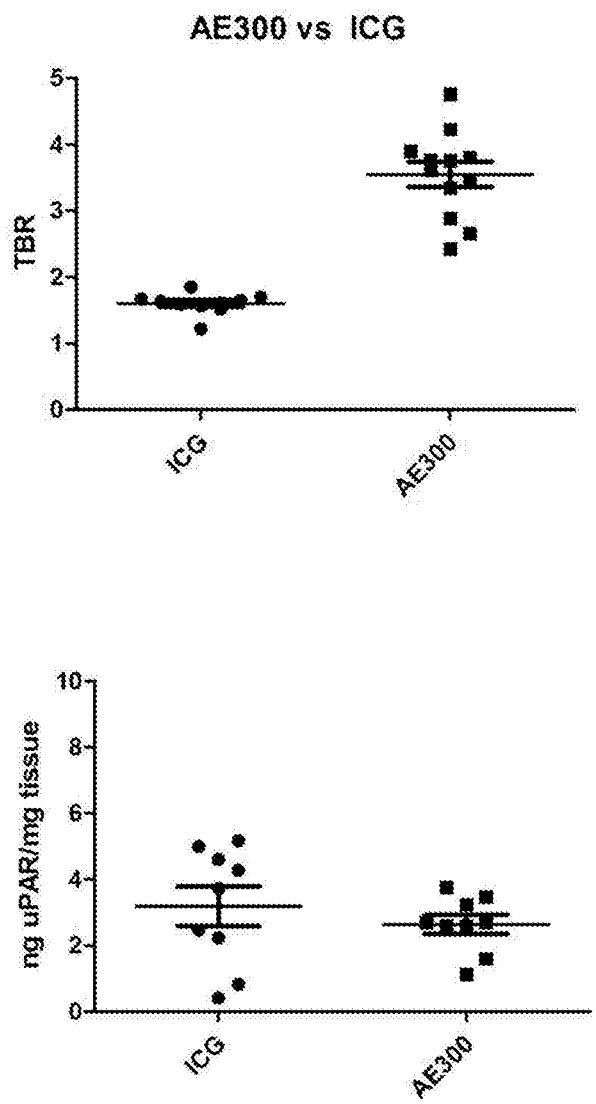
FIG. 4 shows quantitative analysis of the tumor and background uptake.

A group of mice were scanned 15 hr post injection with ICG-Glu-Glu-AE105 in the IVIS Lumina XR. A high uptake in the tumor was observed (FIG. 3) and quantitative analysis of the tumor and background uptake, resulted in a tumor-to-background (TBR) ratio of 3.52±0.167 (n=10) (FIG. 4a). The max radiance for the tumors was in the range 3.43E+08±0.34E+08 radiance efficiency.

Next, a group of mice were imaged with only ICG in order to validate the specificity of the new probe. No specific uptake was seen in the tumor. TBR for ICG was 1.04±0.04 (n=10) (The max radiance for the tumors were in the range 7.51E+06±3.13E+05). All tumors from both groups of mice were subsequently resected after the last scan and the uPAR expression in the tumor lysate was analysed. uPAR expression level was identical in each group (3.19±0.59 for ICG and 2.64±0.28 for ICG-Glu-Glu-AE105) (FIG. 4a).

Figure 5:
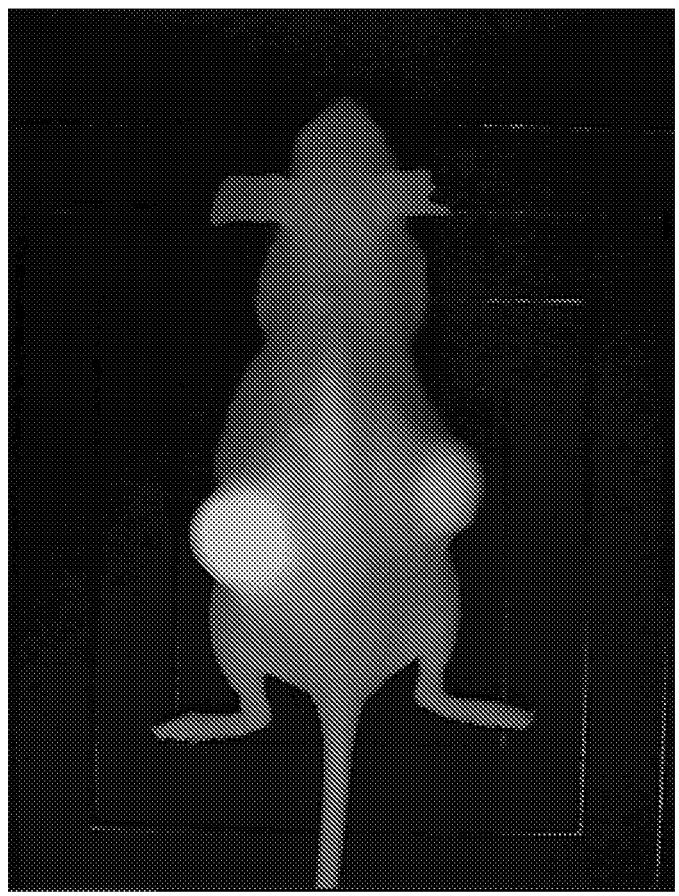
FIG. 5 shows photographs of tumor scans with the compound of the invention using Fluorobeam®.

Finally, to delineate the translational use of this method, the group of mice injected with ICG-Glu-Glu-AE105 was also imaged with the clinically approved camera Fluobeam® (FIG. 5). Clear tumor identification was possible due to high uptake of ICG-Glu-Glu-AE105 as seen in FIG. 5. This imaging modality gave similar TBR (3.58±0.29) as the IVIS Lumina XR and thus confirms the translational potential of ICG-Glu-Glu-AE105.

Data Interpretation

Intraoperative optical imaging with NIR is a new emerging technique that can help surgeons remove solid tumours with higher accuracy and decrease the number of patient with positive margins. In this study, the newly synthesised probe ICG-Glu-Glu-AE105 was characterized in vitro and in vivo in a human glioblastoma xenograft mouse model.

Many designs of optical probes have been constructed. Several groups have investigated probes targeting the EGFR receptor[9], integrin $\alpha_v\beta_3$ [10] and HER1 and HER2 [11]. Numerous probes are based on antibodies as targeting vectors because of the ease of conjugating them to fluorophors and the well-known high affinity for the target. However, a number of limitations in using antibodies for in vivo optical imaging are present. The size of an antibody influences the pharmacological profile, and result in a long plasma half-life which again results in a high background and decrease the potential TBR value. An acceptable TBR value is therefore only achievable 1-3 days after injection [9, 12], thus limiting the clinical usefulness and thereby the translation potential. If smaller peptides are used an optimal imaging timepoint can get as low as 3-6 hours after injection as a result of faster clearing time. In the present study, a scan time 15 hrs post injection was found to be optimal for the peptide-based probe, thus providing a clinical useful application where a patient would be injected in the evening before planned surgery the next day.

The conjugated fluorophor is also an important choice to make. There exist numerous fluorophors in the NIR window with different properties. It was chosen to use ICG since it is the most often-used fluorophor because of its long history in angiographies, It is FDA approved and has a well-established safety profile, thus paving the way for a more easy clinical translation. The fluorescent properties of ICG has been passed by other upcoming fluorophors such as IRDye 800CW. This newer developed fluorophor exhibit features as higher brightness, easier conjugation and hydrophilicity. Especially the hydrophobicity of ICG seems to be an important feature considering the reduction in binding affinity found in this study due to conjugation of ICG, where both the size and high hydrophobicity seems to be responsible for this observation. One potential solution to this observation could be to use a longer linker and/or a more hydrophilic linker such as PEG. This approach has been done with success by others [13]. However, the limited safety profile and no clinical data for IRDye 800CW in contrast to ICG, makes any clinical translation difficult in near future. Translation of a new probe from preclinical studies to the clinical bed is with an approved fluorophor as ICG more advantageous. However the linker is not only for protection of the peptide. Several studies [13] have shown that conjugation of ICG to an antibody decrease the fluorescent signal from ICG. A comparison of ICG and ICG-Glu-Glu-AE105 showed a 2-fold decrease in fluorescence intensity for the conjugated probe (data not shown). A group have though shown that quenching of ICG is eliminated when the probe interact with cells [11], due to internalization and degradation of the conjugated vector. The ICG molecule is released and de-quenched. This property can be exploited in vivo where the non-internalized circulating probe has lower fluorescence intensity than the targeted internalized probe. ICG have primarily been used for delineating malignant glioblastomas. However, ICG has only been used in excessive doses were macroscopic colouration of the tissue have delineated the tumour and the fluorescent properties have been neglected. Further, this delineation of the tumour is most likely a result of the EPR effect and not a tumour specific accumulation.

Several targets for optical imaging in cancer detection have been investigated and both endogenous and exogenous fluorophors has shown great potential for clinical translation. Conversion of 5-ALA to PpIX, an endogenous fluorescent process, has been shown to occur in excess in glioblastomas and have reached clinical studies with convincing results. An advantage uPAR, as target, holds over 5-ALA is the information given regarding the tumors phenotype. uPAR has been correlated with a poor prognosis and aggressive metastatic behavior. Further uPAR have shown to be expressed in the invasive front of the tumor and in the surrounding stroma. This makes uPAR an ideal target for NIR intraoperative optical resection of solid tumors. In addition the receptor need to be over expressed on the surface of the cancer cells. This has been confirmed by flowcytometry for the glioblastoma cell line used in this human xenograft model.

The main aim was to develop a targeted ICG probe, with high affinity and specificity towards uPAR and high in vivo stability. Results from this study have shown that the newly developed probe ICG-Glu-Glu-AE105 possesses all these properties. Conjugated to the clinical approved fluorophor ICG the use of this probe in intra-operative imaging has a high clinical translation potential.

REFERENCES

1. Pogue B W, Gibbs-Strauss S L, Valdés P A, et al. Review of Neurosurgical Fluorescence Imaging Methodologies. IEEE J Select Topics Quantum Electron 16:493-505. doi: 10.1109/JSTQE.2009.2034541
2. Mushawah MD Catherine M Appleton MD Amy E Cyr MD William E Gillanders MD Rebecca L Aft MD PhD Timothy J Eberlein MD Feng Gao PhD Julie A Margenthaler MD Al JABF, Mushawah MD Al F, MD CMA, et al. (2012) Positive margin rates following breast-conserving surgery for stage I-III breast cancer: palpable versus nonpalpable tumors. Journal of Surgical Research 177: 109-115. doi: 10.1016/j.jss.2012.03.045
3. Nguyen Q T, Tsien R Y (2013) Fluorescence-guided surgery with live molecular navigation—a new cutting edge. Nature Publishing Group 1-10. doi: 10.1038/nrc3566
4. Vahrmeijer A L, Hutteman M, van der Vorst J R, et al. (2013) Image-guided cancer surgery using near-infrared fluorescence. Nature Publishing Group 10:507-518. doi: 10.1038/nrclinonc.2013.123
5. Persson M, Madsen J, Østergaard S, et al. (2012) Quantitative PET of human urokinase-type plasminogen activator receptor with 64Cu-DOTA-AE105: implications for visualizing cancer invasion. Journal of Nuclear Medicine 53:138-145. doi: 10.2967/jnumed.110.083386
6. Persson M, Madsen J, Østergaard S, et al. (2012) 68Ga-labeling and in vivo evaluation of a uPAR binding DOTA- and NODAGA-conjugated peptide for PET imaging of invasive cancers. Nuclear Medicine and Biology 39:560-569. doi: 10.1016/j.nucmedbio.2011.10.011
7. Persson M, Liu H, Madsen J, et al. (2013) First 18F-labeled ligand for PET imaging of uPAR: In vivo studies in human prostate cancer xenografts. Nuclear Medicine and Biology 40:618-624. doi: 10.1016/j.nucmedbio.2013.03.001
8. Li Z B, Niu G, Wang H, et al. (2008) Imaging of Urokinase-Type Plasminogen Activator Receptor Expression Using a 64Cu-Labeled Linear Peptide Antagonist by microPET. Clinical Cancer Research 14:4758-4766. doi: 10.1158/1078-0432.CCR-07-4434
9. Day K E, Sweeny L, Kulbersh B, et al. (2013) Preclinical Comparison of Near-Infrared-Labeled Cetuximab and Panitumumab for Optical Imaging of Head and Neck Squamous Cell Carcinoma. Mol Imaging Biol. doi: 10.1007/s11307-013-0652-9
10. Hutteman M, Mieog J S D, van der Vorst J R, et al. (2011) Intraoperative near-infrared fluorescence imaging of colorectal metastases targeting integrin αvβ3 expression in a syngeneic rat model. YEJSO 37:252-257. doi: 10.1016/j.ejso.2010.12.014
11. Ogawa M, Kosaka N, Choyke P L, Kobayashi H (2009) In vivo Molecular Imaging of Cancer with a Quenching Near-Infrared Fluorescent Probe Using Conjugates of Monoclonal Antibodies and Indocyanine Green. Cancer Res 69:1268-1272. doi: 10.1158/0008-5472.CA N-08-3116
12. Ogawa M, Regino C A S, Seidel J, et al. (2009) Dual-Modality Molecular Imaging Using Antibodies Labeled with Activatable Fluorescence and a Radionuclide for Specific and Quantitative Targeted Cancer Detection. Bioconjugate Chem 20:2177-2184. doi: 10.1021/bc900362k
13. Sano K, Nakajima T, Miyazaki K, et al. (2013) Short PEG-Linkers Improve the Performance of Targeted, Activatable Monoclonal Antibody-Indocyanine Green Optical Imaging Probes. Bioconjugate Chem 24:811-816. doi: 10.1021/bc400050k
14. Li Y, Rey-Dios R, Roberts D W, et al. (2014) Peer-Review Reports. World Neurosurgery 1-11. doi: 10.1016/j.wneu.2013.06.014
15. Henricus J. M. Handgraaf, Floris P. R. Verbeek, et al. (2014) Real-time near-infrared fluorescence guided surgery in gynecologic oncology: A review of the current state of the art. Gynecologic Oncology http://dx.doi.org/10.1016/j.ygyno.2014.08.005

The invention claimed is:

1. A fluorophore labeled uPAR-targeting peptide conjugate comprising the formula

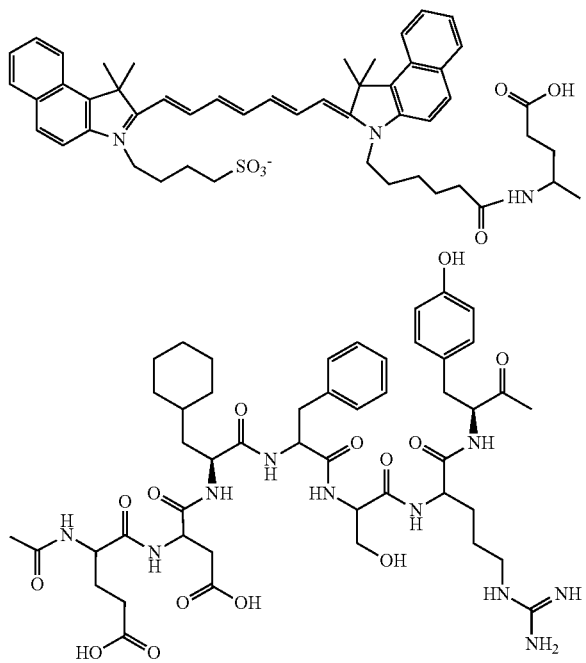

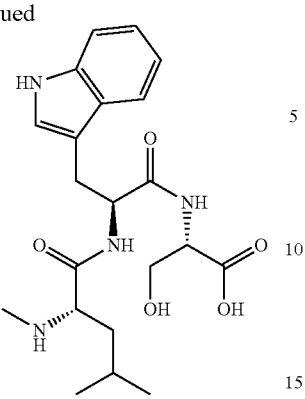

and pharmaceutically acceptable salts thereof.

2. A method of optical imaging of cancer of a subject involving administering a compound of claim 1 to the subject and generating an optical image of at least a part of the subject to which said compound has distributed.

3. Method of claim 2, wherein the compound of claim 2 is administered to the subject in a dose of 0.1-1000 mg per subject.

* * * * *